United States Patent
Shih et al.

(10) Patent No.: US 8,647,282 B2
(45) Date of Patent: Feb. 11, 2014

(54) APPARATUS AND METHOD FOR MEASURING BLOOD PRESSURE WITH MOTION ARTIFACTS ELIMINATION

(75) Inventors: Yi-Cheng Shih, Chiayi (TW); Shih-Chieh Yen, Taipei County (TW)

(73) Assignee: Quanta Computer Inc., Tao Yuan Shien (TW)

( * ) Notice: Subject to any disclaimer, the term of this patent is extended or adjusted under 35 U.S.C. 154(b) by 830 days.

(21) Appl. No.: 12/831,406

(22) Filed: Jul. 7, 2010

(65) Prior Publication Data

US 2011/0054331 A1 Mar. 3, 2011

(30) Foreign Application Priority Data

Sep. 3, 2009 (TW) ............................... 98129625 A

(51) Int. Cl.
*A61B 5/0225* (2006.01)
(52) U.S. Cl.
USPC ........... 600/494; 600/481; 600/485; 600/490; 600/493
(58) Field of Classification Search
USPC .......................... 600/481, 485, 490–496, 500
See application file for complete search history.

(56) References Cited

U.S. PATENT DOCUMENTS

| 4,638,810 | A | * | 1/1987 | Ramsey et al. | 600/494 |
|---|---|---|---|---|---|
| 7,462,152 | B2 | * | 12/2008 | Kolluri et al. | 600/490 |
| 2003/0060720 | A1 | * | 3/2003 | Lee et al. | 600/490 |
| 2006/0116588 | A1 | * | 6/2006 | Archibald et al. | 600/494 |
| 2008/0234589 | A1 | | 9/2008 | Riobo Aboy | |
| 2009/0062663 | A1 | | 3/2009 | Friedman | |
| 2009/0118628 | A1 | | 5/2009 | Zhou | |

FOREIGN PATENT DOCUMENTS

CN 1524491 9/2004
CN 101340845 1/2009

OTHER PUBLICATIONS

English Abstract of CN101340845.
English Abstract of CN1524491.

* cited by examiner

*Primary Examiner* — Patricia Mallari
*Assistant Examiner* — Michael Catina
(74) *Attorney, Agent, or Firm* — McClure, Qualey & Rodack, LLP

(57) ABSTRACT

The invention discloses an apparatus and method for measuring a blood pressure. In particular, the method and apparatus according to the invention are capable of eliminating motion artifacts induced by, for example, talking, irregular breathing, frequent swallowing, coughing, shaking, and so on motions of a subject. The method and apparatus according to the invention utilizes a set of fuzzy logic rules and a curve-fitting way to eliminate the motion artifacts.

6 Claims, 7 Drawing Sheets

APPARATUS AND METHOD FOR MEASURING BLOOD PRESSURE WITH MOTION ARTIFACTS ELIMINATION

CROSS-REFERENCE TO RELATED APPLICATION

This utility application claims priority to Taiwan Application Serial Number 098129625, filed Sep. 3, 2009, which is incorporated herein by reference.

BACKGROUND OF THE INVENTION

1. Field of the Invention

The invention relates to an apparatus and method for measuring a blood pressure. In particular, the method and apparatus according to the invention are capable of eliminating motion artifacts induced by talking, irregular breathing, frequent swallowing, coughing, shaking, and so on motions of a subject.

2. Description of the Prior Art

Blood pressure is a physical phenomena caused from cardiovascular activity.

Because the change in modern diet and lifestyle, it results in increasing the probability of suffering from high blood pressure. Therefore, long-term and regular self-monitoring of blood pressure in hypertensive patient has become an important daily routine because of the hypertension is a chronic disease.

With the progress of science and technology, blood pressure measurement has been developed of is from early invasive blood pressure measurement to current non-invasive blood pressure measurement. The so-called invasive blood pressure measurement is to insert a sensor and a cardiac catheter into a blood vessel to measure the internal pressure of the blood vessel. However, the invasive blood pressure measurement must be practiced with the cooperation of blood catheter surgery. Obviously, the invasive blood pressure measurement is very inconvenient especially for patients need to be measured frequently. Therefore, the development of non-invasive blood pressure measurement is another goal of blood pressure measurement. The non-invasive blood pressure measurement usually uses a mercury sphygmomanometer to measure blood pressure by judging sound during measurement. However, mercury sphygmomanometers may cause environmental pollution. Therefore, in recent years, mercury sphygmomanometers have been gradually phased out over the world, and been replaced by electronic sphygmomanometers.

Most of electronic sphygmomanometers utilize a cuff to be attached to a patient's arm over the brachial artery. The cuff is first inflated to a pressure that is high enough to substantially occlude the brachial artery. The cuff is then deflated slowly. As the pressure of cuff reduces, blood flowing through the brachial artery beneath the cuff increases gradually, and pulse and blood pressure signals enhance gradually.

When the blood flows through the brachial artery accompanying with each contraction of the heart, it imparts a pulsatile motion to the wall of the artery. These pulsatile motions are coupled to the cuff extending over the artery as minute changes in the cuff pressure, which are known as oscillometric pulses. The electronic sphygmomanometer automatically measures and records the amplitude of the oscillometric pulses at a number of cuff pressures. As shown in FIG. 1, after the blood pressure measurement had been completed, a table containing the oscillometric pulse amplitudes recorded at each cuff pressure is obtained.

In theory, the systolic, diastolic, and mean arterial blood pressures can then be determined from the values in the table using experimental definitions of these parameters as a function of the oscillometric pulses amplitudes. For example, as shown in FIG. 2, it is a blood pressure measurement of particular table recording a number of cuff pressures and the oscillometric pulse amplitudes at each cuff pressure. In FIG. 2, the mean arterial blood pressure is determined by the maximum oscillometric pulse amplitude and the cuff pressure measured with the maximum oscillometric pulse amplitude at the same time. The systolic pressure and diastolic pressure are determined experimentally by mean arterial blood pressure of the oscillometric pulse amplitude multiplied respectively by the first ratio and the second ratio.

However, blood pressure measurements are often adversely affected by artifact, generally induced by motions of a subject, such as talking, irregular breathing, frequent swallowing, coughing, shaking, and so on. As shown in FIG. 3, motion-induced artifacts can substantially alter the measured amplitude of oscillometric pulses, and thus introduce inaccuracies in the measurement of the subject's blood pressure.

Accordingly, one aspect of the invention is to provide an apparatus and method for measuring a blood pressure. In particular, the method and apparatus according to the invention are capable of eliminating motion artifacts induced by motions of a subject.

In addition, references point out that effect on aforesaid first ratio and second ratio to determine the systolic pressure and the diastolic pressure includes the arm circumference of subject. Accordingly, another aspect of the invention is to provide an apparatus and method for measuring a blood pressure. In particular, the method and apparatus according to the invention are capable of measuring the arm circumference of subject to accurately determine the first ratio and the second ratio to calculate the systolic pressure and the diastolic pressure.

SUMMARY OF THE INVENTION

An apparatus for measuring a blood pressure, according to a preferred embodiment of the invention, includes a cuff, an inflating unit, a pressure transducer and a controlling/processing unit. The cuff is placed around a subject's arm containing an artery. The inflating unit is coupled to the cuff, and functions inflating the cuff. The pressure transducer is coupled to the cuff. The controlling/processing unit is respectively coupled to the cuff, the inflating unit and the pressure transducer. The controlling/processing unit is for controlling the inflating unit to inflate the cuff to an initial inflation pressure. The controlling/processing unit controls the cuff to be deflated from the initial inflation pressure. The controlling/processing unit obtains a cuff pressure signal and a sequence of raw oscillometric pulse amplitudes relating to counter-pressure of the artery from the pressure transducer as the cuff is deflated from the initial inflation pressure. The controlling/processing unit applies a set of fuzzy logic rules to the raw oscillometric pulse amplitudes to calculate the respective weight for each of the raw oscillometric pulse amplitudes. The controlling/processing unit corrects each of the raw oscillometric pulse amplitude by use of the raw oscillometric pulse amplitudes neighboring said one raw oscillometric pulse amplitude and having weights higher than the threshold to obtain a sequence of current oscillometric pulse amplitudes replacing the raw oscillometric pulse amplitudes. The controlling/processing unit determines the maximum oscillometric pulse amplitude among the current oscillometric pulse amplitudes. The controlling/processing unit determines a systolic pressure relating to the blood pressure of the subject based on the maximum oscillometric pulse amplitude, the cuff pressure signal and the first ratio, and determines a diastolic pressure relating to the blood pressure of the subject based on the maximum oscillometric pulse amplitude, the cuff pressure signal and the second ratio.

According to another preferred embodiment of the invention, the apparatus for measuring the blood pressure further includes a measuring device coupled to the controlling/processing unit and disposed in the cuff for measuring a circumference value relating to the subject's arm. The controlling/processing unit includes a lookup table and obtains the circumference value from the measuring device. The controlling/processing unit determines the first ratio and the second ratio in accordance with the circumference value and the lookup table.

A method for measuring a blood pressure, according to a preferred embodiment of the invention, uses a cuff placed around an arm of a subject containing an artery. The method for measuring the blood pressure according to the invention, firstly, is to inflate the cuff to an initial inflation pressure. Then, the method for measuring the blood pressure according to the invention is to obtain a cuff pressure signal and a sequence of raw oscillometric pulse amplitudes relating to counter-pressure of the artery from a pressure transducer coupled to the cuff as the cuff is deflated from the initial inflation pressure. Next, the method for measuring the blood pressure according to the invention is calculate the respective weight for each of the raw oscillometric pulse amplitudes by applying a set of fuzzy logic rules to the raw oscillometric pulse amplitudes. Afterward, the method for measuring the blood pressure according to the invention is to correct each of the raw oscillometric pulse amplitudes by use of the raw oscillometric pulse amplitudes neighboring the one raw oscillometric pulse amplitude and having weights higher than the threshold to obtain a sequence of current oscillometric pulse amplitudes replacing the raw oscillometric pulse amplitudes. Then, the method for measuring the blood pressure according to the invention is to determine the maximum oscillometric pulse amplitude among the current oscillometric pulse amplitudes. Final, the method for measuring the blood pressure according to the invention is to determine a systolic pressure relating to the blood pressure of the subject based on the maximum oscillometric pulse amplitude, the cuff pressure signal and a first ratio, and to determine a diastolic pressure relating to the blood pressure of the subject based on the maximum oscillometric pulse amplitude, the cuff pressure signal and a second ratio.

The advantage and spirit of the invention may be understood by the following recitations together with the appended drawings.

BRIEF DESCRIPTION OF THE APPENDED DRAWINGS

FIG. 1 illustratively shows a relationship curve got in a typical measurement of blood pressure where the horizontal axis represents time and the vertical axis represents the cuff pressure and the oscillometric pulse as.

Figure 5A:
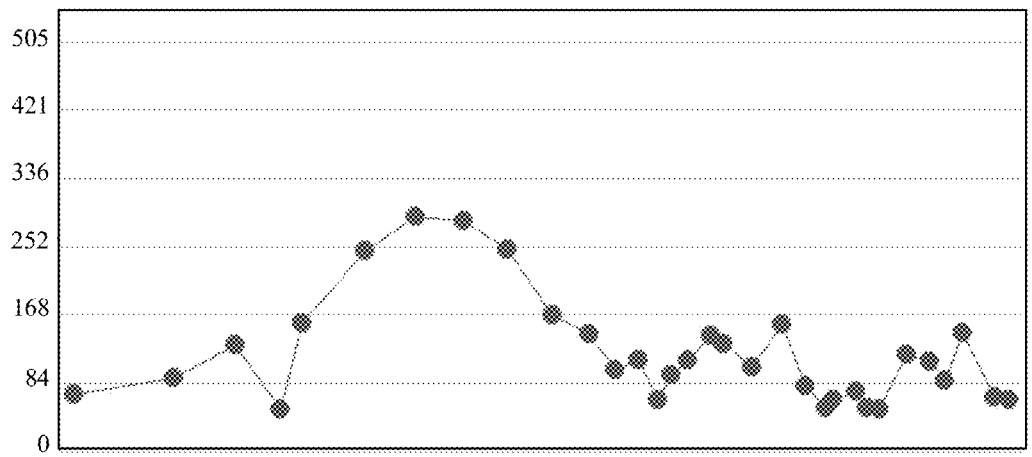

FIG. 5A illustratively shows data of a sequence of raw oscillometric pulse amplitudes measured by using the apparatus for measuring the blood pressure according to the preferred embodiment of the invention.

Figure 5B:
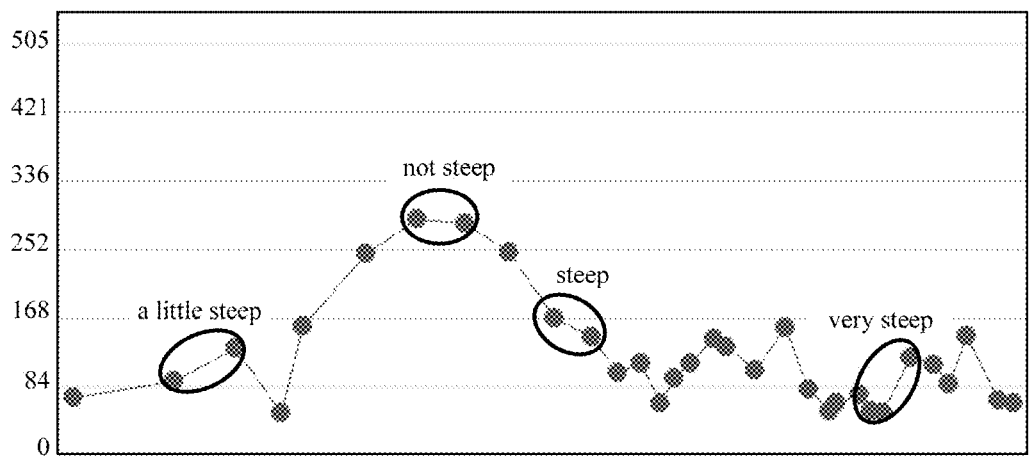

FIG. 5B is a schematic diagram showing four features of the slope derived from connecting two adjacent raw oscillometric pulse amplitudes shown in FIG. 5A.

Figure 5C:
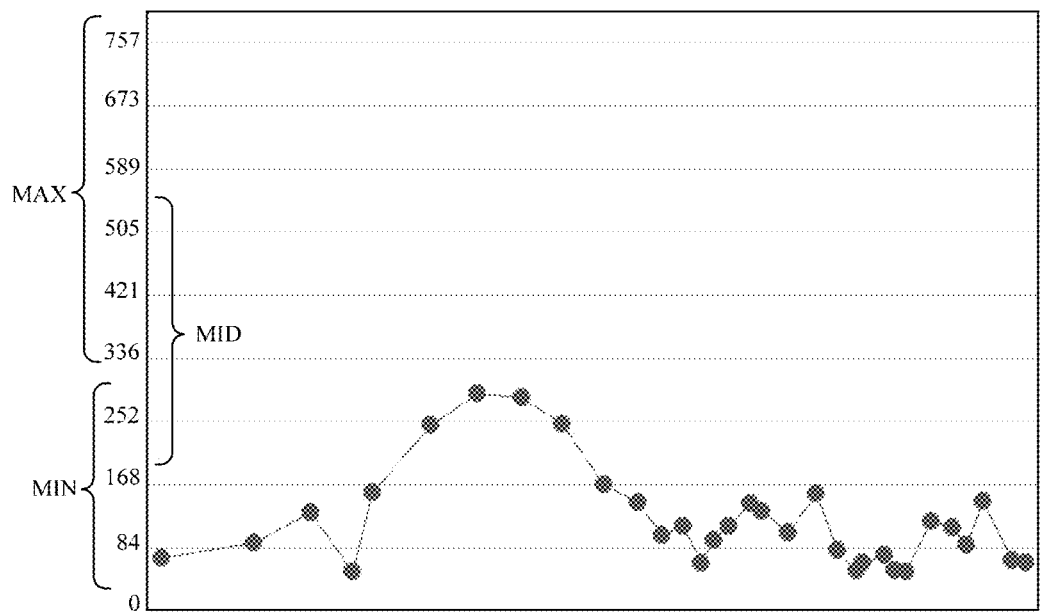

FIG. 5C is a schematic diagram showing that oscillometric pulse amplitudes shown in FIG. 5A are divided into three overlapping ranges including MAX, MID, and MIN.

Figure 5D:
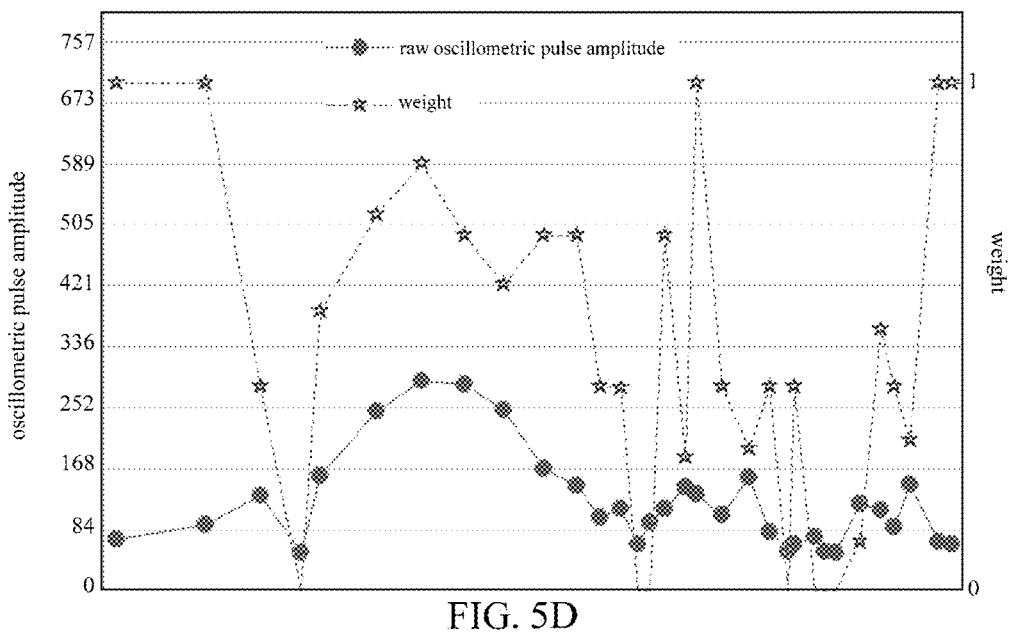

FIG. 5D illustratively shows the raw oscillometric pulse amplitudes shown in FIG. 5A and the calculated weights for the raw oscillometric pulse amplitudes.

Figure 5E:
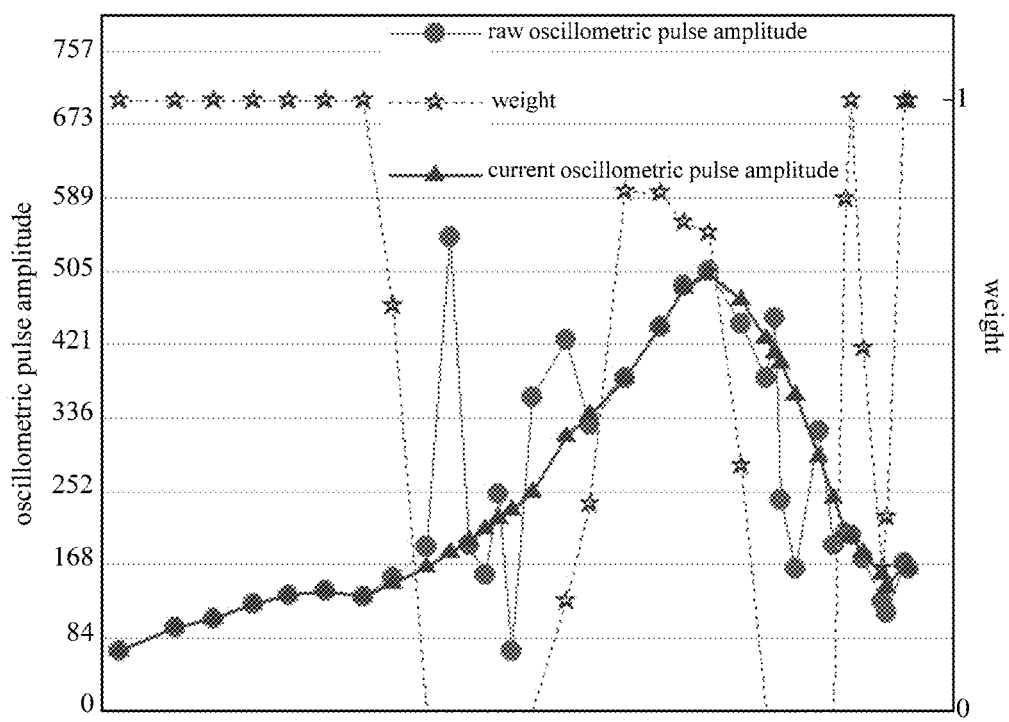

FIG. 5E illustratively shows that a measurement case obtains a sequence of raw oscillometric pulse amplitudes, calculated weights for the raw oscillometric pulse amplitudes and current oscillometric pulse amplitudes acquired by correcting the raw oscillometric pulse amplitudes.

Figure 6:
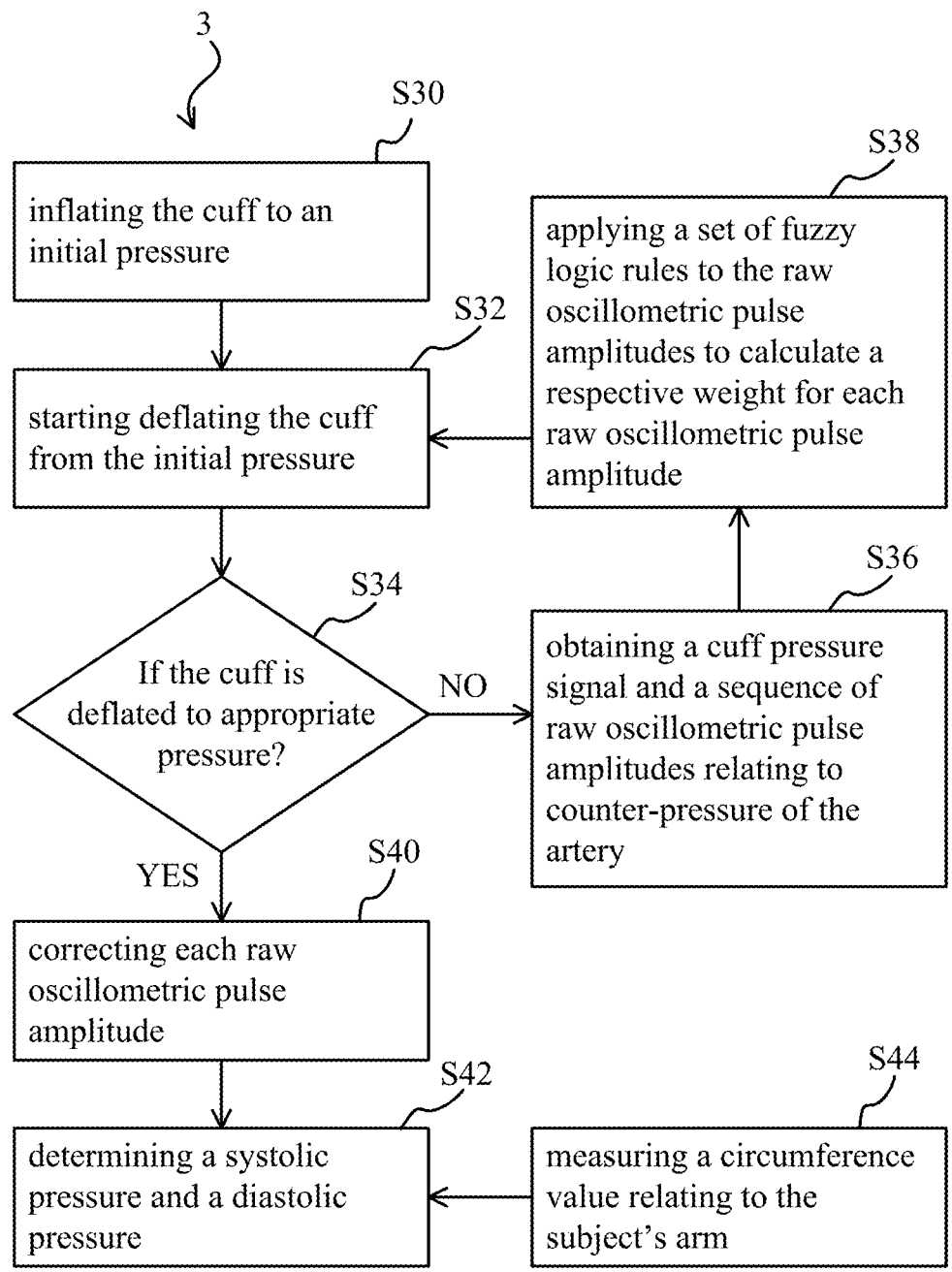

FIG. 6 is a flow chart illustrating a method for measuring a blood pressure according to a preferred embodiment of the invention.

DETAILED DESCRIPTION OF THE INVENTION

Figure 4:
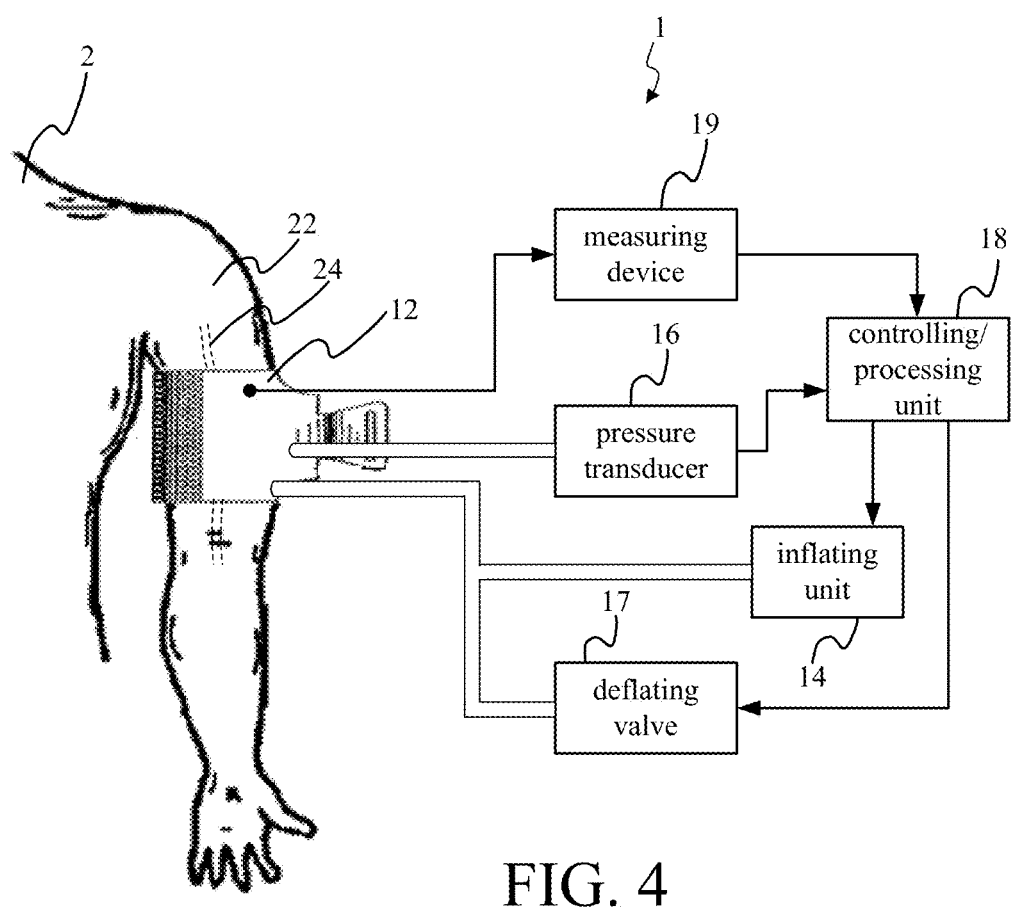
FIG. 4 is a schematic diagram showing architecture of an apparatus for measuring a blood pressure according to a preferred embodiment of the invention.

Please refer to FIG. 4. FIG. 4 is a schematic diagram showing architecture of an apparatus 1 for measuring a blood pressure according to a preferred embodiment of the invention. FIG. 4 also shows a subject 2 and the subject's arm 22 to be measured the blood pressure.

As shown in FIG. 4, the apparatus 1 for measuring a blood pressure according to the invention includes a cuff 12, an inflating unit 14, a pressure transducer 16 and a controlling/processing unit 18.

The cuff 12 is placed around the subject's arm 22 containing an artery 24 as shown in FIG. 4.

Similarly as shown in FIG. 4, the inflating unit 14 is coupled to the cuff 12, and functions inflating the cuff 12. The pressure transducer 16 is coupled to the cuff 12. The controlling/processing unit 18 is respectively coupled to the cuff 12, the inflating unit 14 and the pressure transducer 16. As shown in FIG. 4, the direction of arrow represents the direction of signal transmission and system control, and the hollow tube represents the connection of air tube.

The controlling/processing unit 18 is for controlling the inflating unit 14 to inflate the cuff 12 to an initial inflation pressure. In one embodiment, the inflating unit 14 is a pump.

The controlling/processing unit 18 is also used to control the cuff 12 to deflate from the initial inflation pressure. For example, as shown in FIG. 4, just like a typical electronic sphygmomanometer, the cuff 12 therein is equipped with a deflating valve 17 coupled to the controlling/processing unit 18, and the controlling/processing unit 18 is able to control of the deflating valve 17 to open to deflate and depressurize the cuff 12.

Data processes regarding measured blood pressure data by the apparatus 1 for measuring the blood pressure according to the invention refer to relative data diagrams shown in FIGS. 5A to 5C. As the cuff 12 is deflated and depressurized from the initial inflation pressure, the controlling/processing unit 18 obtains a cuff pressure signal and a sequence of raw oscillometric pulse amplitudes relating to counter-pressure of the artery 24 from the pressure transducer 16 coupled to the cuff 12, as shown in FIG. 5A. The cuff pressure signal is not shown in FIG. 5A, and the dot marks are transformed data of the sequence of raw oscillometric pulse amplitudes rather than pressure values. In FIG. 5A, each of the raw oscillometric pulse amplitudes corresponds to the cuff pressure measured at the same time.

Afterward, the controlling/processing unit 18 applies a set of fuzzy logic rules to the raw oscillometric pulse amplitudes to calculate the respective weight for each of the raw oscillometric pulse amplitudes. Setting of the fuzzy logic rules can be considered from the feature of slope of lines connecting two or more neighboring or non-neighboring raw oscillometric pulse amplitudes, or the feature of included angle formed by connecting lines between three neighboring raw oscillometric pulse amplitudes. For instant, the example disclosed in FIG. 5B shows the slopes of lines connecting two neighboring raw oscillometric pulse amplitudes and the four features of slopes marked by circles: "a little steep", "not steep", "steep", and "very steep".

Figure 1:
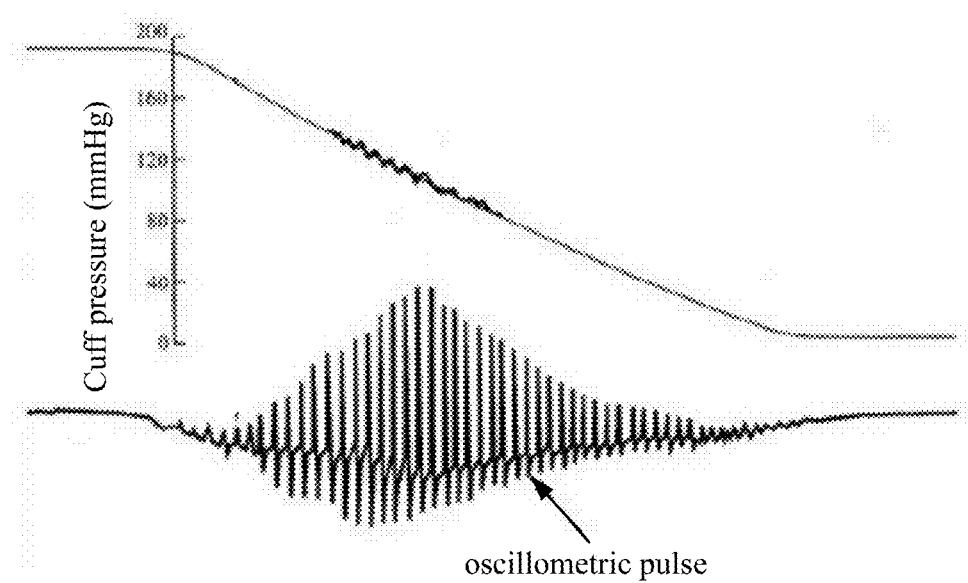
Figure 2:
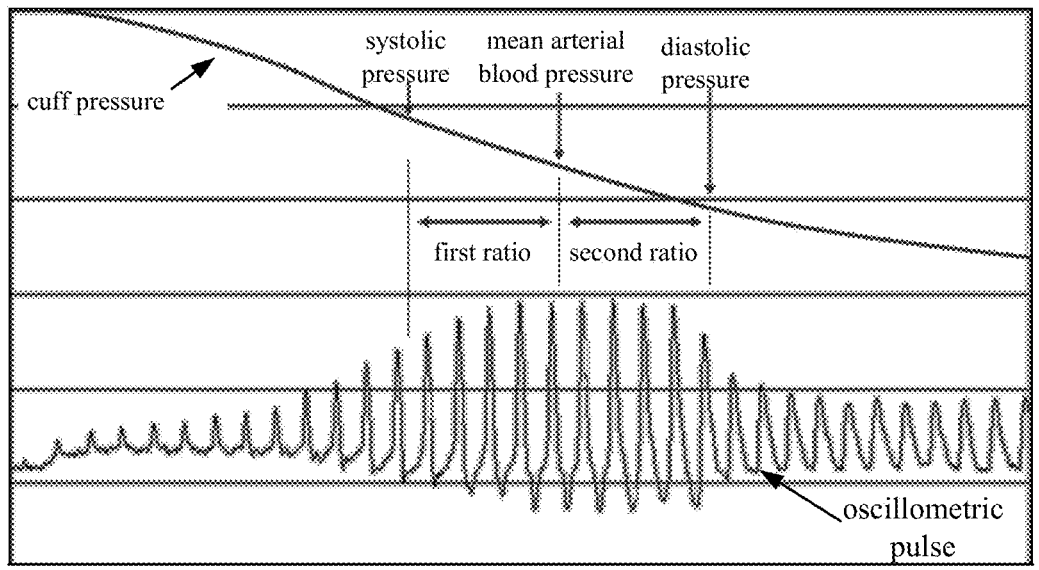
FIG. 2 is a schematic diagram illustrating that the oscillometric pulses of the cuff pressure relationship curve are used to determine the mean arterial blood pressure, the systolic pressure and the diastolic pressure.
Figure 3:
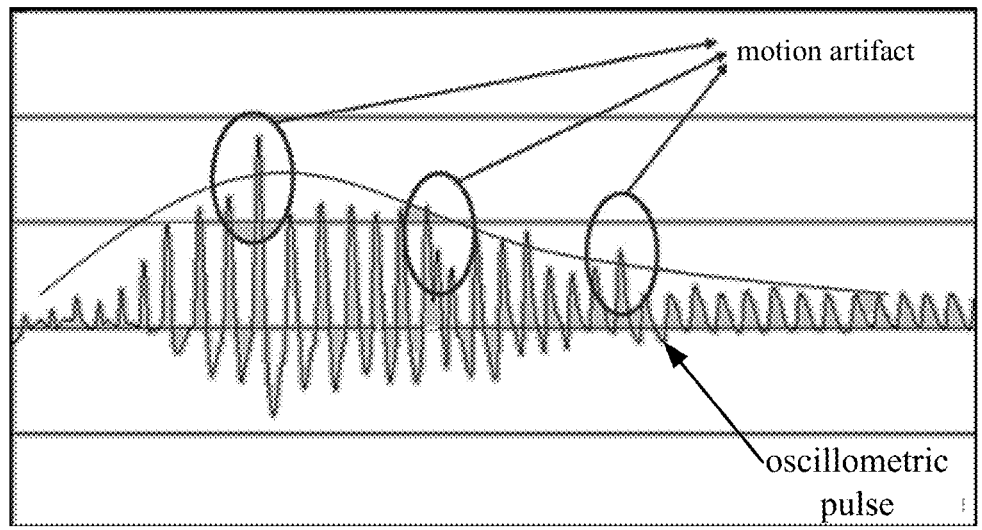
FIG. 3 is a schematic diagram showing the measured oscillometric pulses with motion artifacts induced.

Setting of the fuzzy logic rules can also be considered from the feature of range of pulse amplitudes of the raw oscillometric pulse amplitudes. For example, as shown in FIG. 5C, the pulse amplitudes of the raw oscillometric pulse amplitudes are divided into three overlapping ranges including MAX, MID, and MIN. Then, the pulse amplitudes of the raw oscillometric pulse amplitudes are judged to belong which one of the three ranges. Division of three overlapping ranges (MAX, MID, and MIN) meet the feature of distribution of the pulse amplitudes of the raw oscillometric pulse amplitudes, and three ranges are considered in judgment if one of the raw oscillometric pulse amplitudes is affected by the artifacts induced by motions. Referring to FIG. 2 and FIG. 5 simultaneously, the feature of pulse amplitudes of the measured blood pressure in the range marked MID means that the pulse amplitudes fluctuate severely. Therefore, the raw oscillometric pulse amplitudes are not considered as being affected by the artifacts induced by motions if their pulse amplitudes are in the range marked MID and their slopes are in a higher slope range being set. The raw oscillometric pulse amplitudes are considered as being affected by the artifacts induced by motions if their pulse amplitudes are in the range marked MID and their slopes are higher or lower than the higher slope range being set. On the contrary, the feature of pulse amplitudes of the measured blood pressure in the ranges marked MIN or MAX means that the pulse amplitudes fluctuate tenderly. The raw oscillometric pulse amplitudes are considered as being affected by the artifacts induced by motions if their pulse amplitudes are in the ranges marked MIN or MAX and their slopes are higher than a lower slope range being set.

For the input signals (the cuff pressure signal and the raw oscillometric pulse amplitudes), firstly, they are calculated membership for their individual features. When the membership values of the input signals are obtained, the membership values are applied in the set of fuzzy logic rules to calculate respective weight for each of the raw oscillometric pulse amplitudes. The so-called weight represents reliability for the raw oscillometric pulse amplitude with the weight, that is, the probability of judging if the raw oscillometric pulse amplitude is affected by the artifacts induced by motions. Specifically, the higher weight means the probability that the raw oscillometric pulse amplitude is affected by the motion-induced artifacts is lower, that is, the reliability of the raw oscillometric pulse amplitude with the higher weight is higher, and therefore, the raw oscillometric pulse amplitude with the higher weight is to be corrected slightly in the next process. The lower weight means the probability that the raw oscillometric pulse amplitude is affected by the motion-induced artifacts is higher, that is, the reliability of the raw oscillometric pulse amplitude with the lower weight is lower, and therefore, the raw oscillometric pulse amplitude with the lower weight is to be corrected significantly in the next process.

According to characteristics of general blood pressure signal waveforms without motion-induced artifacts, at least twenty-six fuzzy logic rules can be defined. The following are definitions of some fuzzy logic rules taken as examples:

"If Amplitude is Min and Slope is Not Steep (NS), weight=1";

"If Amplitude is Min and Slope is Very Steep (VS), weight=0";

"If Amplitude is Mid and Slope is Not Steep (NS), weight=0.7";

"If Amplitude is Mid and Slope is A Little Steep (ALS), weight=1";

"If Amplitude is Mid and Slope is Very Steep (VS), weight=0";

"If Amplitude is Max and Slope is Not Steep (NS), weight=1";

"If Amplitude is Max and Slope is A Little Steep (ALS), weight=0.4"; and

"If Amplitude is Max and Slope is Very Steep (VS), weight=0".

As shown in FIG. 5D, the dot marks are the sequence of raw oscillometric pulse amplitudes, and the star marks are the weights respectively calculated for each of the raw oscillometric pulse amplitudes. The weight of each of the raw oscillometric pulse amplitudes is between 0 and 1.

Next, the controlling/processing unit 18 corrects each of raw oscillometric pulse amplitudes by use of the raw oscillometric pulse amplitudes, neighboring said one raw oscillometric pulse amplitude, having weights higher than a threshold to calculate the target oscillometric pulse amplitude corresponding to said one raw oscillometric pulse amplitude. That is, the raw oscillometric pulse amplitudes with higher reliability, neighboring each of raw oscillometric pulse amplitudes, are used to calculate or judge real pulse amplitude of said one raw oscillometric pulse amplitude if without motion-induced artifacts (target oscillometric pulse amplitude). It is to obtain a sequence of current oscillometric pulse amplitudes replacing the raw oscillometric pulse amplitudes in accordance with the corresponding target oscillometric pulse amplitudes.

In one embodiment of the invention, the controlling/processing unit corrects each of the raw oscillometric pulse amplitudes by use of the raw oscillometric pulse amplitudes neighboring the one raw oscillometric pulse amplitude and having weights higher than the threshold, and calculates the respective target oscillometric pulse amplitude in a curve-fitting way. For example, the raw oscillometric pulse amplitude at time T is corrected by use of the raw oscillometric pulse amplitude of around time T (such as time (T−1) and time (T−2)) having weights higher than the threshold, and the respective target oscillometric pulse amplitude at time T is calculated in first-order polynomial way, a second-order polynomial way, or other curve-fitting way. If the raw oscillometric pulse amplitude at time (T−1) has weight lower than the threshold, it is backward to apply the raw oscillometric pulse amplitude at time (T−2). This backward procedure is repeated until the weight of the applied raw oscillometric pulse amplitude is lower than the threshold. Similarly, if the raw oscillometric pulse amplitude at time (T+1) has weight lower than the threshold, it is forward to apply the raw oscillometric pulse amplitudes at time (T+2). This forward procedure is repeated until the weight of the applied raw oscillometric pulse amplitude is higher than the threshold. It needs to be explained that number and relative interval of the applied raw oscillometric pulse amplitudes with weights higher than the threshold prior to time T are uncertainly the same as those of the applied raw oscillometric pulse amplitudes with weights higher than the threshold post time T. For example, it could apply one raw oscillometric pulse amplitude with weight higher than the threshold prior to time T and two raw oscillometric pulse amplitudes with weights higher than the threshold post time T. Finally, the respective target oscillometric pulse amplitude at time T is calculated with three raw oscillometric pulse amplitudes applied above.

The controlling/processing unit 18 calculates the current oscillometric pulse amplitude (OA) replacing the raw oscillometric pulse amplitude (OA) by the following formula:

$$\text{current } OA = \omega \times \text{raw } OA + (1-\omega) \times \text{target } OA \quad (1),$$

where $\omega$ represents the weight of the oscillometric pulse amplitude.

By formula (1), it is explained that the raw oscillometric pulse amplitudes with higher weights are to be corrected slightly, that is, the raw oscillometric pulse amplitudes with relatively higher weights and the target oscillometric pulse amplitudes with relatively lower weights are retained. The raw oscillometric pulse amplitudes with lower weights are to be corrected significantly, that is, the raw oscillometric pulse amplitudes with relatively lower weights and the target oscillometric pulse amplitudes with relatively higher weights are retained.

Referring to FIG. 5E, FIG. 5E illustratively shows that a sequence of raw oscillometric pulse amplitudes (dot marks) are acquired after measurement of a blood pressure by the apparatus 1 for measuring a blood pressure according to the invention, each of the raw oscillometric pulse amplitudes is calculated by applying a set of fuzzy logic rules to obtain the respective weight (star marks), and the raw oscillometric pulse amplitudes are corrected in a second-order polynomial way and by the formula (1) to obtain the current oscillometric pulse amplitude (triangle marks).

Finally, the controlling/processing unit 18 determines the maximum oscillometric pulse amplitude among the current oscillometric pulse amplitudes. And, the controlling/processing unit 18 determines a systolic pressure relating to the blood pressure of the subject 2 based on the maximum oscillometric pulse amplitude, the cuff pressure signal and the first ratio, and determines a diastolic pressure relating to the blood pressure of the subject 2 based on the maximum oscillometric pulse amplitude, the cuff pressure signal, and the second ratio. That is, the controlling/processing unit 18 takes the cuff pressure measured with the maximum oscillometric pulse amplitude at the same time as the mean arterial blood pressure, gets the systolic pressure by multiplying the oscillometric pulse amplitude of the mean arterial blood pressure by the first ratio, and gets the diastolic pressure by multiplying the oscillometric pulse amplitude of the mean arterial blood pressure by the second ratio.

Referring to FIG. 4, according to another preferred embodiment of the invention, the apparatus 1 for measuring the blood pressure further includes a measuring device 19, coupled to the controlling/processing unit 18 and disposed in the cuff 12, for measuring a circumference value relating to the subject's arm 22. The controlling/processing unit 18 includes a lookup table, and acquires the circumference value of the arm 22 from the measuring device 19. The controlling/processing unit 18 accurately determines the first ratio for calculating the systolic pressure and the second ratio for calculating the diastolic pressure in accordance with the circumference value and the lookup table.

Referring to FIG. 6, FIG. 6 is a flow chart illustrating a method 3 for measuring a blood pressure according to a preferred embodiment of the invention. The method 3 for measuring the blood pressure utilizes a cuff to measure a blood pressure of a subject. The cuff is placed around the subject's arm containing an artery.

As shown in FIG. 6, the method 3 for measuring the blood pressure according to the invention, firstly, performs step S30 to inflate the cuff to an initial inflation pressure.

Afterward, the method 3 for measuring the blood pressure according to the invention performs step S32 to deflate the inflated cuff from the initial inflation pressure. Next, the method 3 for measuring a blood pressure according to the invention performs step S34 to detect if the cuff is deflated to the proper pressure. As the cuff is deflated from the initial inflation pressure, the controlling/processing unit starts to record the data of a sequence of raw oscillometric pulse amplitudes.

Once the controlling/processing unit judges that the sample number of a sequence of raw oscillometric pulse amplitudes is enough to start calculating the systolic pressure and the diastolic pressure, the cuff is deflated to the proper pressure. On the other hand, the deflated speed of cuff is controlled by the controlling/processing unit, and the recording rate of the raw oscillometric pulse amplitudes per second is controlled by the controlling/processing unit too. Therefore, it can be estimated that the controlling/processing unit has recorded enough number of the raw oscillometric pulse amplitudes when the cuff is deflated to a certain pressure.

If the detecting result of step S34 is NO, the method 3 for measuring the blood pressure according to the invention performs step S36 to keep the cuff being deflated. And a cuff pressure signal and a sequence of raw oscillometric pulse amplitudes relating to counter-pressure of the artery are obtained from the pressure transducer as the cuff is deflated from the initial inflation pressure. After step S36, the method 3 for measuring the blood pressure according to the invention performs step S38 to apply a set of fuzzy logic rules to the raw oscillometric pulse amplitudes to calculate the respective weight for each of the raw oscillometric pulse amplitudes. After step S36, the method 3 for measuring the blood pressure according to the invention repeatedly performs step S32.

If the detecting result of step S34 is YES, the method 3 for measuring the blood pressure according to the invention performs step S40 to correct each of the raw oscillometric pulse amplitudes by use of the raw oscillometric pulse amplitudes neighboring said one raw oscillometric pulse amplitude and having weights higher than the threshold to obtain a sequence of current oscillometric pulse amplitudes replacing the raw oscillometric pulse amplitudes. The embodiment regarding the correction of the raw oscillometric pulse amplitudes has been described in detail above, and it will not be described in detail again.

Finally, the method 3 for measuring the blood pressure according to the invention performs step S42 to define the maximum oscillometric pulse amplitude among the current oscillometric pulse amplitudes. The method 3 for measuring the blood pressure according to the invention determines a systolic pressure relating to the blood pressure of the subject based on the maximum oscillometric pulse amplitude, the cuff pressure signal, and the first ratio, and determines a diastolic pressure relating to the blood pressure of the subject based on the maximum oscillometric pulse amplitude, the cuff pressure signal, and the second ratio. In other words, the cuff pressure measured with the maximum oscillometric pulse amplitude at the same time is taken as the mean arterial blood pressure. The systolic pressure is determined by multiplying the mean arterial blood pressure of the oscillometric pulse amplitude by the first ratio. The diastolic pressure is determined by multiplying the mean arterial blood pressure of the oscillometric pulse amplitude by the second ratio.

Similarly as shown in FIG. 6, the method 3, according to another preferred embodiment of the invention, for measuring the blood pressure further includes step 44 to obtain the circumference value relating to the subject's arm from the measuring device disposed in the cuff. In step S42, the first ratio and the second ratio are determined according to the circumference value and the lookup table pre-established.

To sum up, the apparatus and method for measuring a blood pressure according to the invention are capable of eliminating motion artifacts induced by motions of the subject. The apparatus and method according to the invention are capable of measuring the arm circumference of subject to accurately determine the purpose of calculating the systolic pressure relating to the first ratio and the diastolic pressure relating to the second ratio.

With the example and explanations above, the features and spirits of the invention will be hopefully well described. Those skilled in the art will readily observe that numerous modifications and alterations of the device may be made while retaining the teaching of the invention. Accordingly, the above disclosure should be construed as limited only by the metes and bounds of the appended claims.

What is claimed is:

1. An apparatus for measuring a blood pressure of a subject susceptible to noise during measurement, comprising:
   a cuff configured to be placed around the subject's arm containing an artery;
   an inflating unit, coupled to the cuff, for inflating the cuff;
   a pressure transducer coupled to the cuff; and
   a controlling/processing unit, coupled to the cuff, the inflating unit and the pressure transducer, respectively, for controlling the inflating unit to inflate the cuff to an initial inflation pressure, controlling the cuff to be deflated from the initial inflation pressure, obtaining a cuff pressure signal and a sequence of raw oscillometric pulse amplitudes (raw OA) relating to counter-pressure of the artery from the pressure transducer as the cuff is deflated from the initial inflation pressure, calculating a respective weight $\omega$ for each of the raw oscillometric pulse amplitudes, the respective weight $\omega$ being indicative of level of noise corresponding to the raw oscillometric pulse amplitude and being obtained based on variation rate of oscillometric pulse amplitudes neighboring to each raw oscillometric pulse amplitude, modifying each of the raw oscillometric pulse amplitudes based on the respective weight $\omega$ to obtain a sequence of current oscillometric pulse amplitudes (current OA) replacing the raw oscillometric pulse amplitudes, defining a maximum oscillometric pulse amplitude among the current oscillometric pulse amplitudes, determining a systolic pressure relating to the blood pressure of the subject based on the maximum oscillometric pulse amplitude, the cuff pressure signal and a first ratio, and determining a diastolic pressure relating to the blood pressure of the subject based on the maximum oscillometric pulse amplitude, the cuff pressure signal and a second ratio, wherein the controlling/processing unit modifies each of the raw oscillometric pulse amplitudes (raw OA) by the steps of:
   utilizing the raw oscillometric pulse amplitudes neighboring said one raw oscillometric pulse amplitude (OA) having respective weights higher than a threshold value to calculate a respective target oscillometric pulse amplitude (target OA) in a curve-fitting way; and
   calculating the current oscillometric pulse amplitude (current OA) by the following formula:

$$\text{current } OA = \omega \times \text{raw } OA + (1-\omega) \times \text{target } OA.$$

2. The apparatus of claim 1, further comprising a measuring device, coupled to the controlling/processing unit and disposed in the cuff, for measuring a circumference value relating to the subject's arm wherein the controlling/processing unit comprises a lookup table, obtains the circumference value from the measuring device, and determines the first ratio and the second ratio in accordance with the circumference value and the lookup table.

3. The apparatus of claim 1, wherein the controlling/processing unit applies a set of fuzzy logic rules to the raw oscillometric pulse amplitudes to calculate the respective weight $\omega$ for each of the raw oscillometric pulse amplitudes.

4. A method for measuring a blood pressure of a subject susceptible to noise during measurement by use of a cuff configured to be placed around the subject's arm containing an artery, said method comprising the steps of:
   inflating the cuff to an initial inflation pressure by an inflating unit;
   obtaining a cuff pressure signal and a sequence of raw oscillometric pulse amplitudes relating to counter-pressure of the artery from a pressure transducer coupled to the cuff as the cuff is deflated from the initial inflation pressure;
   calculating a respective weight $\omega$ for each of the raw oscillometric pulse amplitudes by a processor unit, the respective weight $\omega$ being indicative of level of noise corresponding to the raw oscillometric pulse amplitude and being obtained based on variation rate of oscillometric pulse amplitudes neighboring to each raw oscillometric pulse amplitude;
   based on the respective weight $\omega$, modifying each of the raw oscillometric pulse amplitudes to obtain a sequence of current oscillometric pulse amplitudes replacing the raw oscillometric pulse amplitudes by the processor unit, wherein the processing unit modifies each of the raw oscillometric pulse amplitudes (raw OA) by the steps of:
   utilizing the raw oscillometric pulse amplitudes neighboring said one raw oscillometric pulse amplitude (OA) having respective weights higher than a threshold value to calculate a respective target oscillometric pulse amplitude (target OA) in a curve-fitting way; and
   calculating the current oscillometric pulse amplitude (current OA) by the following formula:

$$\text{current } OA = \omega \times \text{raw } OA + (1-\omega) \times \text{target } OA;$$

defining a maximum oscillometric pulse amplitude among the current oscillometric pulse amplitudes by the processor unit; and
   based on the maximum oscillometric pulse amplitude, the cuff pressure signal, a first ratio and a second ratio, determining a systolic pressure and a diastolic pressure relating to the blood pressure of the subject by the processor unit.

5. The method of claim 4, further comprising the steps of:
   obtaining a circumference value relating to the subject's arm the cuff pressure signal from a measuring device in the cuff; and
   determining the first ratio and the second ratio in accordance with the circumference value and a lookup table by the processor unit.

6. The method of claim 4, wherein the step of calculating the respective weight ω for each of the raw oscillometric pulse amplitudes is performed by applying a set of fuzzy logic rules to the raw oscillometric pulse amplitudes.

* * * * *